United States Patent [19]

Neilson et al.

[11] Patent Number: 5,733,319
[45] Date of Patent: Mar. 31, 1998

[54] LIQUID COOLANT SUPPLY SYSTEM

[75] Inventors: Bruce H. Neilson, Brooklyn Park; James V. Kauphusman, Champlin, both of Minn.

[73] Assignee: Urologix, Inc., Minneapolis, Minn.

[21] Appl. No.: 637,405

[22] Filed: Apr. 25, 1996

[51] Int. Cl.$^6$ ............................................. A61F 7/00
[52] U.S. Cl. ........................ 607/105; 607/96; 607/22
[58] Field of Search ........................... 607/96–102, 105, 607/116, 156; 606/20–22, 26, 41; 128/748, 673, 691

[56] References Cited

U.S. PATENT DOCUMENTS

| | | | |
|---|---|---|---|
| 5,300,099 | 4/1994 | Rudie | 607/11 |
| 5,326,343 | 7/1994 | Rudie et al. | 607/101 |
| 5,334,181 | 8/1994 | Rubinsky et al. | 606/22 |
| 5,409,006 | 4/1995 | Buchholtz et al. | 607/96 X |
| 5,417,689 | 5/1995 | Fine | 606/41 |
| 5,423,811 | 6/1995 | Imran et al. | 606/41 |
| 5,470,350 | 11/1995 | Buchholtz et al. | 607/97 |
| 5,472,405 | 12/1995 | Buchholtz et al. | 601/2 |
| 5,476,444 | 12/1995 | Keeling et al. | 604/4 |

FOREIGN PATENT DOCUMENTS 0 597 463 A2   5/1994   European Pat. Off. .

OTHER PUBLICATIONS

Taylor & Francis, "International Journal of Hyperthermia", vol. 11, No. 1, Jan.–Feb. 1995, pp. 95–108.
Declaration of Stephen J. Clark Under 37 CFR § 1.98 and Exhibits A and B attached.
Technical Innovations and Notes, "A Practical System for Clinical Radiofrequency Hyperthermia", Brezovich et al., pp. 423–429.
Journal of Endourology, "Single–Session Transurethral Microwave Thermotherapy for the Treatment of Benign Prostatic Obstruction", S. St. C. Carter et al., pp. 137–144.
Turner: Recent Developments and Work in Progress, "Recent Developments and Work in Progress", P.F. Turner, pp. 422–424.
British Journal of Urology, "Local Hyperthermia of the Prostate Gland for the Treatment of Benign Prostatic Hypertrophy and Urinary Retention – A Preliminary Report", A. Lindner et al., pp. 567–571.

*Primary Examiner*—Jennifer Bahr
*Assistant Examiner*—Ryan Carter

[57] ABSTRACT

A liquid coolant supply system for supplying a liquid coolant to a thermal therapy catheter includes a sensor control unit, a liquid coolant containment unit and mounts. The sensor control unit includes a pump, a cooling device, a temperature sensor and a pressure sensor. The liquid coolant containment unit includes a sealed reservoir, a coolant-sensor interface module and a pump interface fluidly coupled to the thermal therapy catheter. The coolant-sensor interface module includes a body defining a fluid chamber, a temperature interface supported adjacent the fluid chamber within the body, and a pressure interface supported adjacent the fluid chamber within the body. The mounts removably support the sealed reservoir, pump interface, temperature interface and pressure interface of the containment unit adjacent the cooling device, the pump, the temperature sensor and the pressure sensor. The temperature interface communicates a temperature indicant of the liquid coolant circulating through the fluid chamber to the temperature sensor. The pressure interface communicates a pressure indicant of the liquid coolant circulating through the fluid chamber to the pressure sensor. The cooling device and the pump are controlled based upon the sensed temperature and pressure of the liquid coolant.

20 Claims, 6 Drawing Sheets

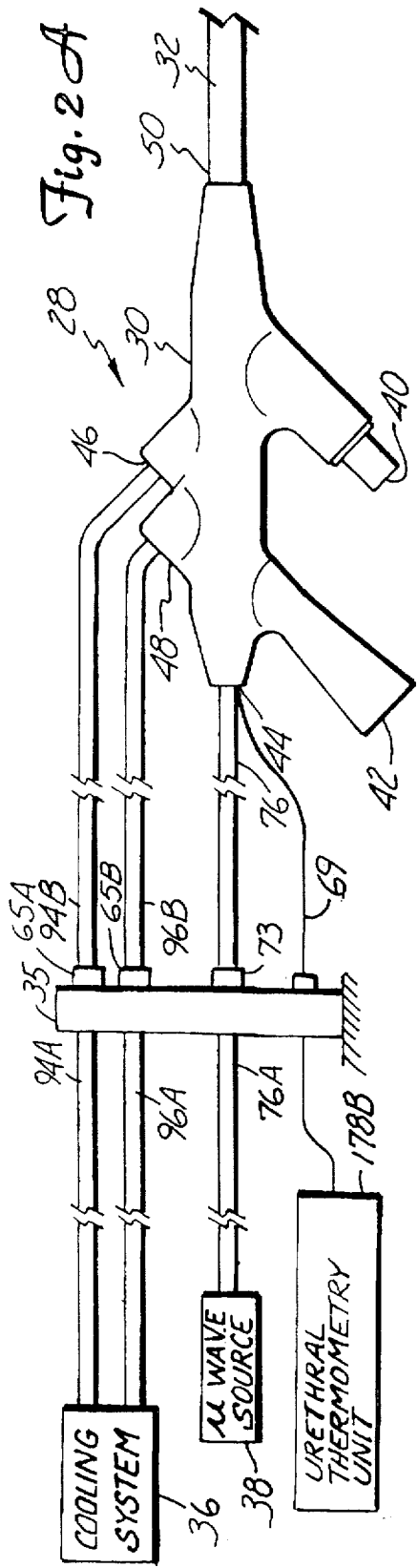
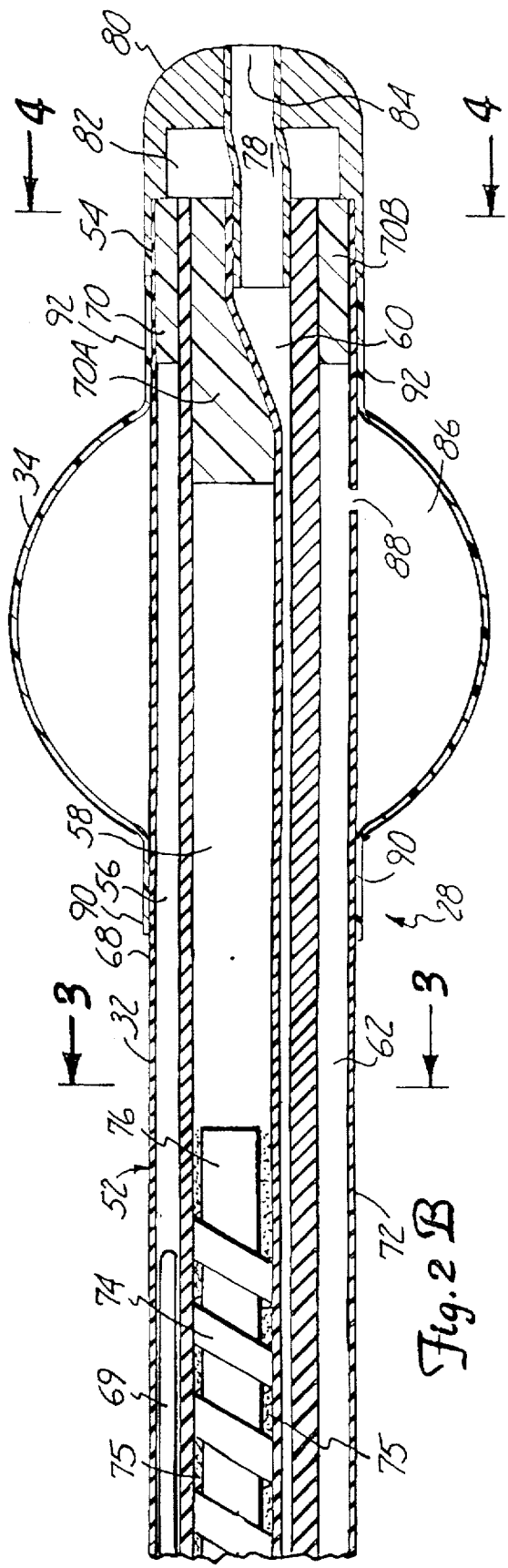

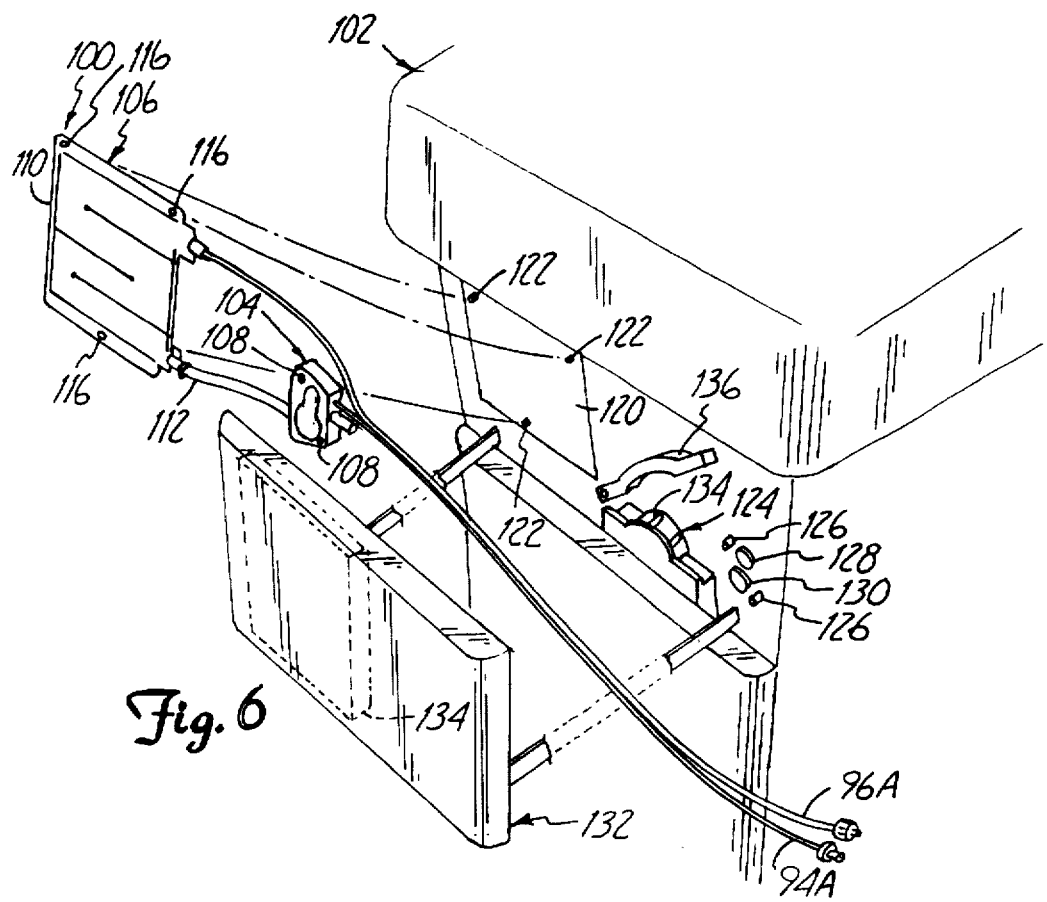
Fig. 6
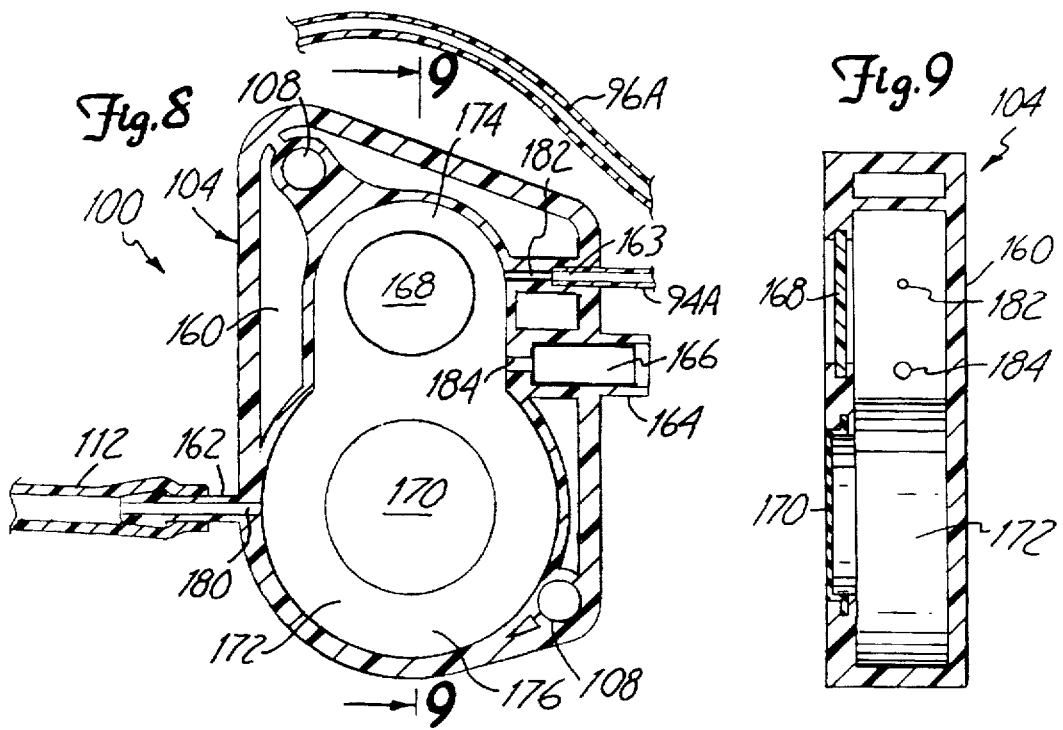
Fig. 8
Fig. 9

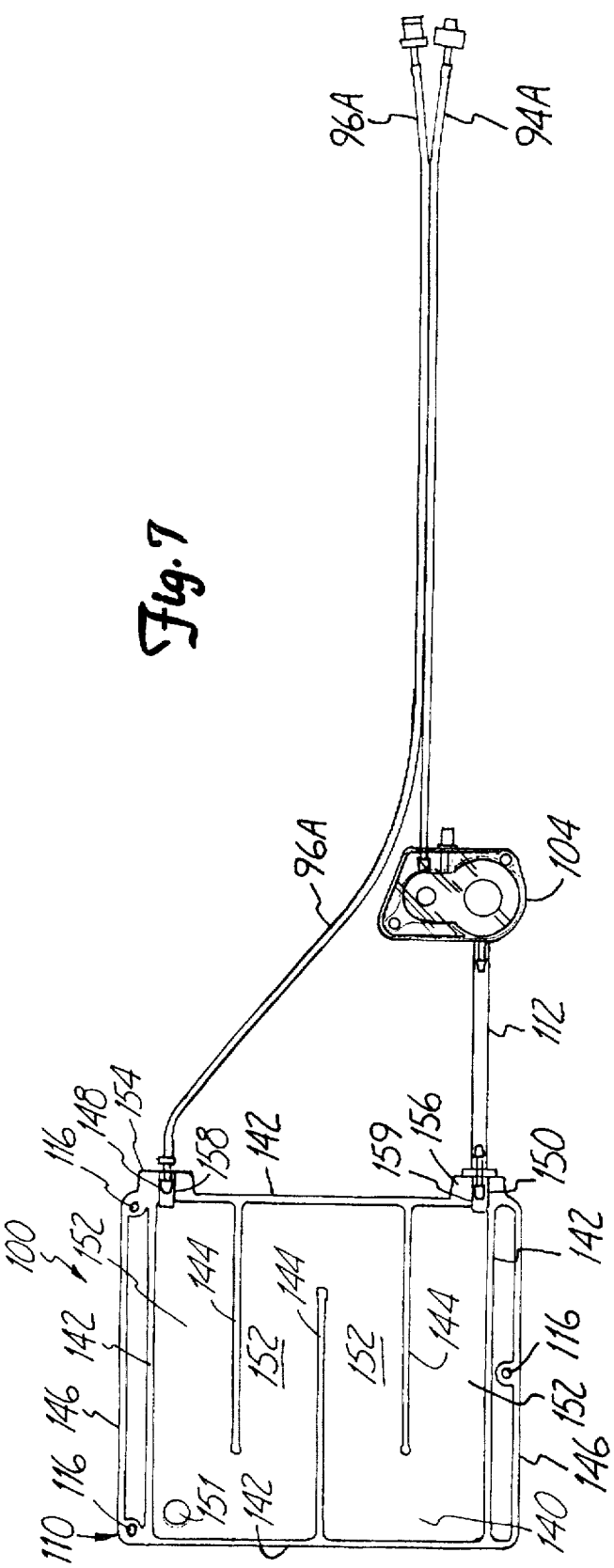

LIQUID COOLANT SUPPLY SYSTEM

BACKGROUND OF THE INVENTION

The present invention relates to field of microwave thermal therapy of tissue. In particular, the present invention relates to a coolant-sensor interface module for enabling temperature and pressure of a liquid coolant within a thermal therapy catheter fluid supply system to be sensed.

Benign prostatic hyperplasia (BPH) may be treated using transurethral thermal therapy as described in further detail in U.S. Pat. No. 5,413,588 entitled DEVICE FOR ASYMMETRICAL THERMAL THERAPY WITH HELICAL DIPOLE MICROWAVE ANTENNA and in U.S. patent application Ser. No. 08/309,137 entitled COOLANT PRE-CHILLING PRIOR TO BENIGN PROSTATIC HYPERPLASIA TREATMENT, both assigned to Urologix, Inc., which are herein incorporated by reference. During transurethral thermal therapy, tumorous tissue growth within the prostate surrounding the urethra is heated to necrose the tumorous tissue to treat BPH. Transurethral thermal therapy is administered by use of a microwave antenna-containing catheter which includes a multi-lumen shaft. Energization of the microwave antenna causes the antenna to emit electromagnetic energy which heats tissue within the prostate. To avoid unnecessary and undesirous damage to the urethral and adjacent healthy tissues, the catheter is provided with cooling lumens through which liquid coolant circulates to control the temperature distribution of tissue surrounding the catheter.

Typically, the liquid coolant is supplied to the thermal therapy catheter by a pump which pumps the liquid coolant from a reservoir through the thermal therapy catheter. Conventional liquid coolant supply systems comprise relatively large reservoirs containing as much as five gallons of liquid coolant from which liquid coolant is supplied to the thermal therapy catheter. The liquid coolant contained within the large reservoir is simply maintained at room temperature. Although the liquid coolant being circulated through the thermal therapy catheter experiences a temperature increase during thermal therapy, such increases are relatively insignificant due to the large volume of liquid contained in the reservoir. However, conventional liquid coolant supply systems have failed to provide for precise, closed loop control of the temperature and pressure of the liquid coolant being supplied to the thermal therapy catheter. In addition, conventional liquid coolant supply systems are expensive and require extensive and time consuming sterilization between a treatment of different patients.

SUMMARY OF THE INVENTION

A coolant-sensor interface module for enabling pressure temperature and pressure of a liquid coolant within a thermal therapy catheter fluid supply system to be sensed by a temperature sensor and a pressure sensor, respectively includes a body, a temperature interface and a pressure interface. The body defines a fluid chamber with an inlet port and an outlet port for allowing the liquid coolant to circulate through the fluid chamber. The temperature interface is supported adjacent the fluid chamber within the body and communicates a temperature indicant of the liquid coolant circulating through the fluid chamber to the temperature sensor. The pressure interface is supported adjacent the fluid chamber within the body and communicates a pressure indicant of the liquid coolant circulating through the fluid chamber to the pressure sensor.

The coolant-sensor interface module of the present invention is preferably incorporated as part of a liquid coolant containment unit which additionally includes a liquid coupling assembly for fluidly connecting the coolant-sensor interface module to inlet and outlet ports of the thermal therapy catheter and for containing the liquid coolant as the liquid coolant is cooled and pumped by cooling and pumping means. Preferably, the liquid coupling assembly includes a sealed reservoir and a pump interface fluidly connected to one another. In the preferred embodiment of the present invention, the sealed reservoir comprises a thin thermally conducting bag having a plurality of winding channels for channeling liquid flow adjacent the cooling means. The pump interface preferably comprises a compressible liquid conduit that is dynamically compressed so that liquid coolant may be circulated with a peristaltic pump.

Lastly, the liquid cooling containment unit incorporating the coolant-sensor interface is preferably utilized as part of a liquid coolant supply system which includes a sensor control unit having a pump, a cooling device, a temperature sensor and a pressure sensor. In the preferred embodiment, the cooling device comprises a flat thermally conducting plate which is temperature controlled based upon temperature sensed by the temperature sensor. The pump of the sensor control unit preferably comprises a peristaltic pump which pumps and circulates the liquid coolant at a flow rate based upon pressure sensed by the pressure sensor. In the preferred embodiment in which the temperature interface is illustrated as a radiation emitter which emits radiation based upon the temperature of the liquid coolant and in which the pressure interface is illustrated as being a flexible diaphragm which expands based upon the pressure of the liquid coolant, the temperature sensor and the pressure sensor of the sensor control unit comprise an infrared radiation sensor and at least one pressure transducer, respectively. To enable the liquid coolant containment unit of the present invention to be easily mounted and removed from the sensor control unit, the sensor control unit includes mounts for removably supporting the reservoir adjacent the cooling plate, the pump interface adjacent the peristaltic pump, and the temperature interface and pressure interface of the sensor interface module adjacent the temperature sensor and pressure sensor of the sensor control unit.

BRIEF DESCRIPTION OF THE DRAWINGS

FIG. 2A is a side view of the distal end of the urethral catheter.

FIG. 2B is an enlarged sectional view of the proximal end of the urethral catheter.

FIG. 6 is a partially exploded perspective view of a cooling system of the present invention.

FIG. 7 is a greatly enlarged side elevational view of a liquid containment unit of the cooling system.

FIG. 8 is a fragmentary side elevational view of the liquid containment unit including a sensor interface module.

FIG. 9 is a cross-sectional view of the sensor interface module taken along line 9—9.

DETAILED DESCRIPTION OF THE PREFERRED EMBODIMENTS

Figure 1:
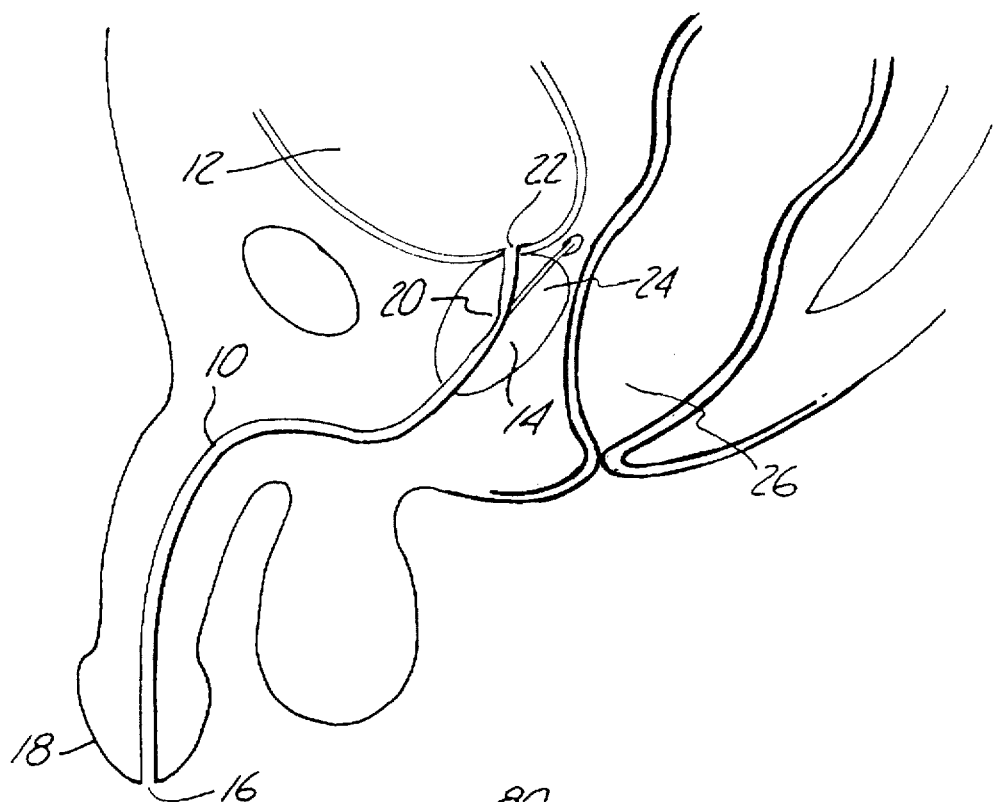
FIG. 1 is a vertical sectional view of a male pelvic region showing the urinary organs effected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) is made possible by microwave antenna-containing catheter 28 of the present invention, which is shown in FIGS. 2A and 2B.

FIG. 2A shows a side view of a distal end of catheter 28. FIG. 2B shows an enlarged sectional view of a proximal end of catheter 28. As shown in FIGS. 2A and 2B, catheter 28 generally includes multi-port manifold 30, multi-lumen shaft 32, shaft position retention balloon 34, connection manifold 35, cooling system 36, microwave generating source 38 and urethral thermometry unit 39.

Multi-port manifold 30 includes inflation port 40, urine drainage port 42, microwave antenna port 44, cooling fluid in port 46 and cooling fluid out port 48. Ports 40-48 communicate with corresponding lumens within shaft 32. Manifold 30 is preferably made of medical-grade silicone sold by Dow Corning under the trademark Silastic Q-7-4850.

Figure 3:
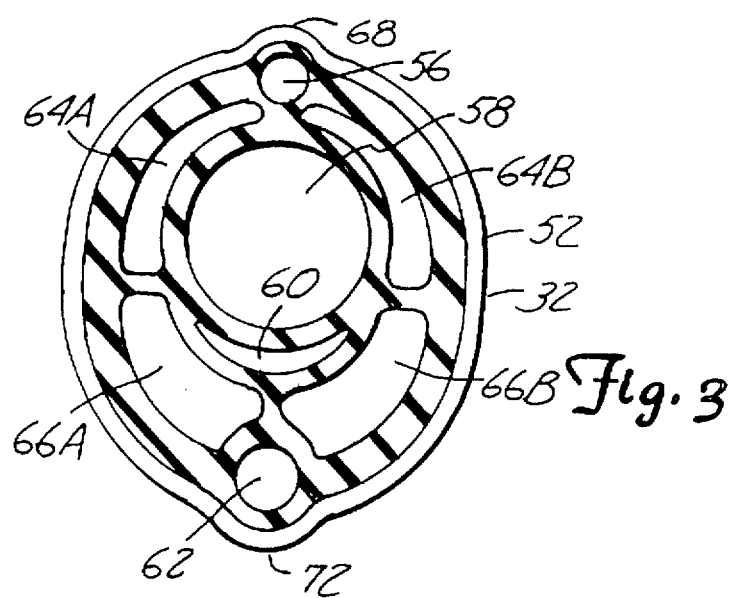
FIG. 3 is a cross-sectional view of the urethral catheter of FIG. 2B taken along line 3—3.

Multi-lumen shaft 32 is connected to manifold 30 at shaft distal end 50. Shaft 32 is a multi-lumen, Foley-type urethral catheter shaft which is extruded from a flexible, medical-grade silicone sold by Dow Corning under the trademark Silastic Q-7-4850. Shaft 32, which has an outer diameter of about 16 French, includes outer surface 52, which is generally elliptical in cross-section as shown in FIG. 3. Shaft 32 is long enough to permit insertion of proximal shaft end 54 through urethra 10 and into bladder 12. In one preferred embodiment, shaft 32 is coated with a hydrophilic solution sold by Hydromer, Inc. under the mark Hydromer, which lubricates outer surface 52 of shaft 32 and facilitates its advancement within urethra 10.

As shown in FIG. 2B-4, shaft 32 includes temperature sensing lumen 56, microwave antenna lumen 58, urine drainage lumen 60, balloon inflation lumen 62, cooling fluid intake lumens 64A and 64B, and cooling fluid exhaust lumens 66A and 66B. Lumens 56-66B generally extend from distal shaft end 50 to proximal shaft end 54.

Temperature sensing lumen 56 is positioned near first side 68 of shaft 32. Temperature sensing lumen 56 communicates with microwave antenna port 44 and permits insertion of thermometry sensor 69 within shaft 32 to monitor the temperature of surrounding tissue when shaft 32 is inserted within urethra 10. Sensor 69 exits through port 44 and is connected through connection manifold 35 to urethral thermometry unit 39. Urethral thermometry unit 39 measures urethral temperature based upon signals from temperature sensor 69 within catheter 28. In a preferred embodiment, thermometry sensor 69 is a fiber optic luminescence type temperature sensor sold by Luxtron Corporation. Temperature sensing lumen 56 is sealed at proximal end 54 by silicone plug 70.

Microwave antenna lumen 58 is eccentric to the longitudinal axis of shaft 32, antenna lumen 58 being positioned nearer first side 68 of shaft 32 than second side 72 of shaft 32. Antenna lumen 58 is sealed at proximal end 54 by silicone plug 70A. At its distal end, antenna lumen 58 communicates with microwave antenna port 44. Microwave antenna 74 is permanently positioned within antenna lumen 58 near balloon 34. Antenna 74 is positioned within antenna lumen 58 so as to be generally situated adjacent the benign tumorous tissue of prostate 14 when shaft 32 is properly positioned within urethra 10. As shown in FIGS. 2A-2B, antenna 74 is bonded within antenna lumen 58 by adhesive bond 75. Antenna 74 is carried at the proximal-most end of coaxial cable 76. The distal-most end of coaxial cable 76 is connected to connection manifold 35 by a conventional quick-coupling fitting 73. Coaxial cable 76 communicates with microwave generating source 38 by connection cable 76A, which is connected between microwave generating source 38 and connection manifold 35. In one embodiment, connection cable 76A is a standard RG 400 coaxial cable. Microwave generating source 38 produces a maximum of 100 watts of electrical power at about 915 MHz frequency, ±13 MHz, which is within the FCC-ISM standards. When antenna 74 is energized by microwave generating source 38, antenna 74 emits electromagnetic energy which causes heating of tissue within prostate 14.

Urine drainage lumen 60 is positioned adjacent antenna lumen 58, between antenna lumen 58 and second side 72. Urine drainage lumen 60 communicates with urine drainage port 42 and defines a drainage path for urine when proximal end 54 of shaft 32 is inserted within bladder 12. Urine drainage lumen 60 is connected to urine drainage lumen extension 78 at proximal end 54. Urine drainage lumen extension 78 is bonded within proximal end cap 80. End cap 80 is further bonded over outer surface 52 of shaft 32 at proximal shaft end 54, with cavity 82 surrounding lumen extension 78. With end cap 80 and urine drainage lumen extension 78 in place, opening 84 to lumen extension 78 permits urine to drain from bladder 12 through urine drainage tureen 60 and out urine drainage port 42 when proximal shaft end 54 is inserted within bladder 12. Drainage of urine from bladder 12 is necessary due to frequent bladder spasms which occur during transurethral thermal therapy.

Balloon inflation lumen 62 is positioned near second side 72, generally between urine drainage lumen 60 and second side 72. Balloon inflation lumen 62 communicates with inflation port 40 and is sealed at proximal end 54 by silicone plug 70B. Balloon inflation lumen 62 communicates with interior 86 of balloon 34 by opening 88.

Figure 5:
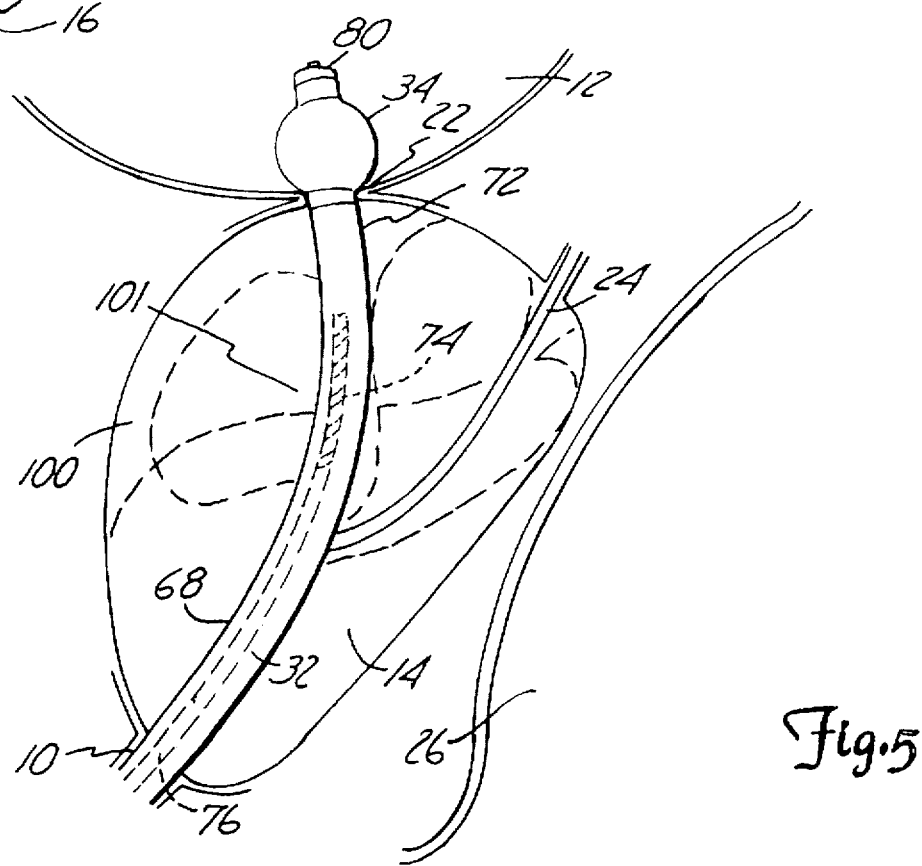
FIG. 5 is an enlarged view of the male pelvic region of FIG. 1 showing the urethral catheter positioned within the prostate region.

Balloon 34, which is formed from a tubular section of a flexible, medical-grade silicone sold by Dow Coming under the trademark Silastic Q-7-4720, is secured over shaft 32 by bonding balloon waists 90 and 92 over exterior surface 52 of shaft 32 near proximal shaft end 54. Balloon 34 is inflated by an inflation device (not shown), which is connected to inflation port 40 and which supplies positive fluid pressure to interior 86 of balloon 34. Balloon 34 is deflated when the inflation device supplies a negative fluid pressure (i.e., a vacuum) to interior 86 of balloon 34. Balloon 34 serves to retain shaft 32 in a fixed position within urethra 10 when balloon 34 is inflated within bladder 12 near bladder neck 22, as shown in FIG. 5.

Figure 4:
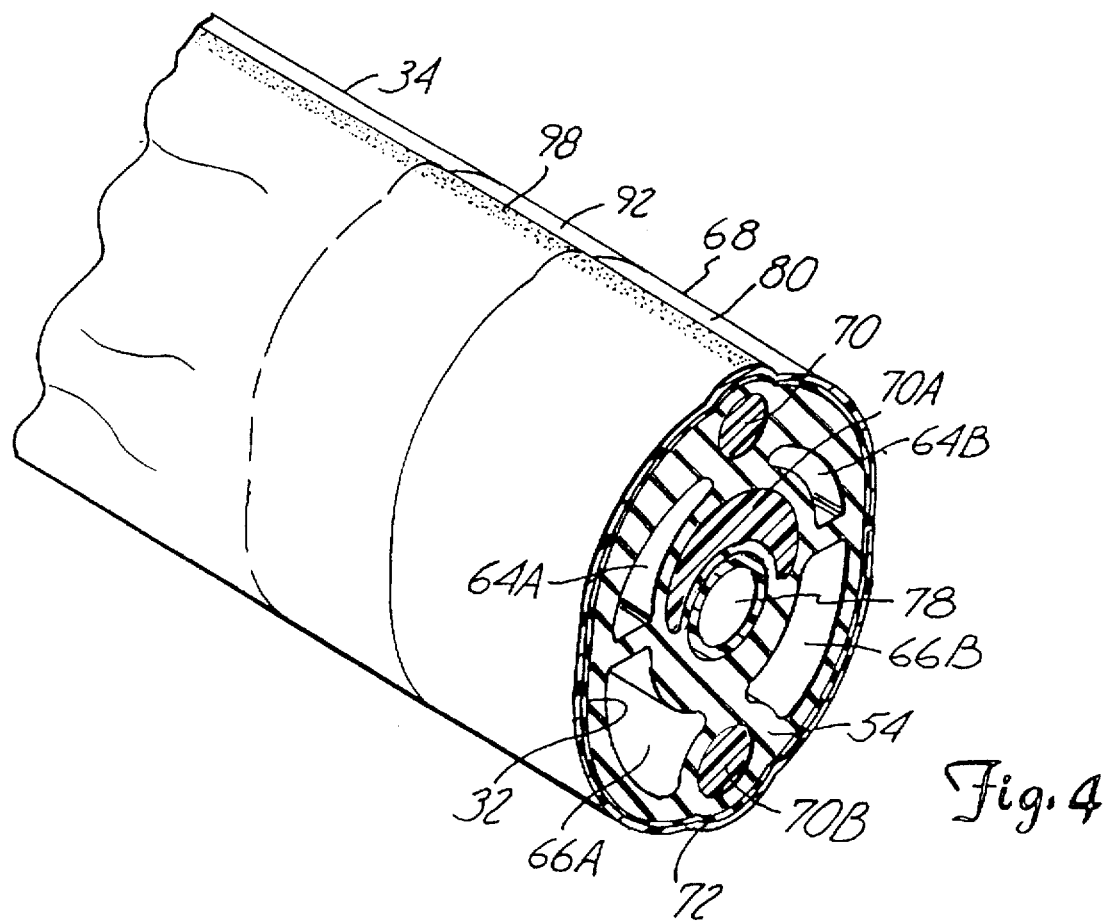
FIG. 4 is a perspective view of a proximal region of the urethral catheter with the end portion taken in section from line 4—4 of FIG. 2B.

As shown in FIG. 2B, FIG. 3 and FIG. 4, cooling fluid intake lumens 64A, 64B are positioned circumjacent first side 68, between first side 68 and antenna lumen 58. Cooling fluid intake lumens 64A, 64B extend from distal shaft end 50 to proximal shaft end 54 where lumens 64A, 64B are exposed to cavity 82 of end cap 80. Intake lumens 64A, 64B are relatively narrow in cross-section and have a relatively small cross-sectional surface area. Water contained within intake lumens 64A, 64B performs two essential functions. First, water contained within lumens 64A, 64B absorbs some of the microwave energy emitted by antenna 74. This assists, in part, in controlling the volume of tissue adjacent first side 68 of shaft 32 that is heated above about 45° C. Second, the water within lumens 64A, 64B absorbs heat energy generated by the microwave energy from adjacent tissues (i.e., urethra 10) via thermal conduction. This prevents the portion of urethra 10 adjacent first side 68 from being overheated and damaged when antenna 74 is energized.

Cooling fluid exhaust lumens 66A, 66B are circumjacent second side 72 with lumens 66A, 66B generally positioned between second side 72 and antenna lumen 58. Like intake lumens 64A, 64B, exhaust lumens 66A, 66B extend from shaft distal end 50 to shaft proximal end 54 where exhaust lumens 66A, 66B are exposed to cavity 82 of end cap 80. Exhaust lumens 66A, 66B are wider in cross-section than intake lumens 64A, 64B, and have a cross-sectional area greater than the cross-sectional area of intake lumens 64A, 64B. Water within exhaust lumens 66A, 66B is therefore capable of absorbing a greater amount of microwave energy when antenna 74 is energized. As a result, for a given power output from microwave generating source 38, the temperature of tissue adjacent second side 72 will remain below about 45° C. Water within exhaust lumens 66A, 66B also absorbs heat energy from adjacent tissue (i.e., urethra 10) when antenna 74 is energized, which prevents the portion of urethra 10 adjacent second side 72 from being overheated and damaged when antenna 74 is energized.

Intake lumens 64A, 64B and exhaust lumens 66A, 66B are supplied with deionized water from cooling system 36. Water from cooling system 36 is chilled and maintained at a temperature of between about 12°–25° C., preferably 12°–15° C., and pumped at a rate of between about 100–150 milliliters per minute via water feed line 94A to connection manifold 35. The water flows through connection manifold 35 to water feed line 94B and to water intake port 46, which communicates with water intake lumens 64A, 64B. Under fluid pressure, the water circulates through intake lumens 64A, 64B to cavity 82 of end cap 80. The water returns to cooling system 36 through exhaust tureens 66A, 66B to fluid exhaust port 48. The water is carried from water exhaust port 48 via water return line 96B to connection manifold 35, and from connection manifold 35 to cooling system 36 via water return line 96A. The water is then re-chilled and re-circulated. Water feed line 94B and water return line 96B are each provided with a conventional quick-coupling fitting 65A and 65B, respectively, which permits catheter 28 to be easily disconnected from cooling system 36.

FIG. 6 is a partially exploded perspective view of cooling system 36. Cooling system 36 generally includes liquid coolant containment unit 100 and sensor control unit 102. Liquid coolant containment unit 100 contains the liquid coolant supplied to catheter 28 by cooling system 36 and generally includes coolant-sensor interface module 104 and liquid coupling assembly 106. Sensor interface module 104 temporarily receives and contains circulating liquid coolant and interfaces between the circulating liquid coolant and sensor control unit 102. Sensor interface module 104 physically isolates the circulating liquid coolant from sensor control unit 102, but enables sensor control unit 102 to sense and detect temperature and flow rate of the liquid coolant circulating through sensor interface module 104. In particular, sensor interface module 104 permits sensor control unit 102 to sense the temperature and the pressure, a parameter corresponding to flow rate, of the liquid coolant circulating through sensor interface module 104. As a result, sensor interface module 104 prevents the circulating liquid coolant from physically contacting sensor control unit 102 while permitting the temperature and flow rate of the circulating fluid to be sensed so that time consuming and expensive cleaning and sterilization of sensor control unit 102 between patients may be eliminated. In addition, sensor interface module 104 permits liquid coolant containment unit 106 to be inexpensively manufactured and renders liquid cooling containment unit 106 disposable, thereby eliminating otherwise necessary cleaning and sterilization of a non-disposable, fixed liquid coolant containment units.

Liquid coupling assembly 106 fluidly connects sensor interface module 104 to water feed line 94B and water return line 96B of thermotherapy catheter 28 (shown in FIG. 2B). In particular, liquid coupling assembly 106 circulates the liquid coolant from water return line 96B into sensor interface module 104 and circulates the liquid coolant from sensor interface module 104 into water feed line 94B of catheter 28. Liquid coupling assembly 106 contains the liquid coolant as the temperature of the liquid coolant is maintained at a desired temperature and pumped by sensor control unit 102. Liquid coupling assembly 106 includes water return line 96A, reservoir 110, pump interface tube 112 and water feed line 94A. Water return line 96A fluidly connects reservoir 110 of liquid coolant containment unit 106 to water return line 96B of catheter 28. Reservoir 110 is fluidly connected between water return line 96A and pump interface tube 112. Reservoir 110 preferably has an enlarged flow passage or flow area with respect to water return line 96a to reduce the flow rate of the liquid coolant through reservoir 110. Reservoir 110 includes mounting holes 116 for releasably mounting reservoir 110 to sensor control unit 102 so that reservoir 110 may be removed from sensor control unit 102 to permit easy replacement of liquid containment 100.

Pump interface tube 112 fluidly connects reservoir 110 and sensor interface module 104. Pump interface tube 112 channels liquid coolant from reservoir 110 into sensor interface module 104. In addition, pump interface tube 112 interfaces with sensor control unit 102 to allow sensor control unit 102 to pump liquid coolant through pump interface tube 112 and to circulate the liquid coolant through liquid coolant containment unit 100. Lastly, water return line 94A carries the liquid coolant from sensor interface module 104 to water return line 94b of catheter 28.

Sensor control unit 102 simultaneously performs multiple functions and includes cooling plate 120, mounts 122, pump 124, mounts 126, temperature sensor 128 and pressure sensor 130. Cooling plate 120 is a generally flat plate of material having a high degree of thermal conductivity, preferably aluminum. The temperature at the surface of cooling plate 120 is regulated by circulating temperature regulated fluid behind and adjacent to the surface of cooling plate 120. Alternatively, the temperature at the surface of cooling plate 120 may be regulated with other well-known conventional heating and cooling means such as refrigeration coils, resistors or the like. Cooling plate 120 cools, as necessary, the liquid coolant circulating through liquid coupling assembly 106. In particular, cooling plate 120 regulates the temperature of the liquid coolant circulating through reservoir 110 by indirect thermal conduction. Because cooling plate 120 does not directly contact the liquid coolant to regulate the temperature of the liquid coolant, sensor control unit 102 remains free from potential contamination concerns and the health risks.

Mounts 122 preferably comprise pins which project sensor control unit 102. Mounts 122 engage mounting openings 116 of reservoir 110 to removably support reservoir 110 adjacent to and in contact with cooling plate 120. As a result, cooling plate 120 is in sufficient contact with reservoir 110 to efficiently regulate the temperature of the liquid coolant circulating through reservoir 110. At the same time, mounts 122 permit reservoir 110 of liquid containment unit 106 to be easily removed and separated from cooling plate 120 of sensor control unit 102. As can be appreciated, mounts 122 may alternatively comprise any one of a variety of releasable mounting mechanisms such as hook and loop fasteners.

Pump 124 preferably comprises a peristaltic pump including rotating roller pins 134 and jaw 136. As is conventionally known, roller pins 134 rotate at a controllable speed. Jaw 132 clamps over and adjacent to roller pins 134 to hold and position a flexible fluid containment structure adjacent the rotating roller pins 134. In the preferred embodiment illustrated, pump interface tube 112 comprises a flexible tube which is positioned between roller pins 134 and jaw 136. Jaw 136 is positioned so as to clamp or hold pump interface tube 112 against roller pins 134. Roller pins 134 at least partially compress the flexible material forming the tube of pump interface tube 112. Rotation of roller pins 134 about a common axis dynamically compresses the flexible material forming the tube of pump interface tube 112 to pump and circulate fluid through and along pump interface tube 112. As a result, pump 124 draws the liquid coolant through water return line 96A and reservoir 110 by creating a vacuum within pump interface tube 112 and simultaneously pumps fluid from pump interface tube 112 into sensor interface module 104 and through water feed line 94A to catheter 28.

Mounts 126 preferably comprise pins which project from sensor control unit 102. Mounts 126 engage mounting detents 108 to removably and releasably support sensor interface module 104 adjacent to temperature sensor 128 and pressure sensor 130. As can be appreciated, mounts 126 may alternatively comprise any one of a variety of releasable mounting mechanisms such as hook and loop.

Temperature sensor 128 preferably comprises a conventional infrared sensor sized to match a corresponding radiation emitter of sensor interface module 104. Temperature sensor 128 senses radiation emitted from the radiation emitter of sensor interface module 104 to determine a corresponding temperature of the liquid coolant circulating through sensor interface module 104. Because temperature sensor 128 senses temperature by sensing or detecting radiation emitted by the radiation emitter of sensor interface module 104, temperature sensor 128 is able to determine the temperature of the liquid coolant circulating through sensor interface module 104 indirectly without directly contacting the liquid coolant. Thus, the need for cleaning and possibly sterilizing temperature sensor 128 between patients is reduced or eliminated.

Pressure sensor 130 comprises a conventionally known pressure transducer. Pressure sensor 130 senses pressure of the liquid coolant circulating through sensor interface module 104. Because pressure is a parameter corresponding to flow rate, pressure sensor 130 enables sensor control unit 102 to determine the flow rate of the liquid coolant through sensor interface module 104. In addition, pressure sensor 130 also enables sensor control unit 102 to determine the flow rate of the liquid coolant through liquid containment unit 100 and through catheter 128. Because pressure sensor 130 indirectly senses pressure and the flow rate of the liquid coolant circulating through sensor interface module 104, temperature sensor 130 avoids contamination and health concerns which otherwise result from direct contact between the sensors and the liquid coolant.

Cover 132 is movably coupled to sensor control unit 102 adjacent cooling plate 120, pump 124, temperature sensor 128 and pressure sensor 130. Cover 132 is a generally flat solid plate which is movable in an opened position and a closed position. In the opened position, cover 132 allows reservoir 110 to be positioned adjacent to cooling plate 120, pump interface tube 112 to be positioned within pump 124, and sensor interface module 104 to be positioned adjacent to temperature sensor 128 and pressure sensor 130. At the same time, in the opened position, cover 132 also allows liquid containment unit 100 to be removed and separated from sensor control unit 102 for replacement of liquid containment unit 100. In the closed position, cover 132 positions and maintains reservoir 110 adjacent cooling plate 120, pump interface tube 112 within pump 124 and sensor interface module 104 adjacent temperature sensor 128 and pressure sensor 130. In the preferred embodiment, cover 132 includes an insulating member 134 made of a thermally insulating material such as Styrofoam. Member 134 is positioned and supported by cover 132 so as to engage reservoir 110 of liquid containment unit 100. In addition to sandwiching reservoir 110 of liquid containment unit 100 between insulating member 134 and cooling plate 120, insulating member 134 insulates the liquid coolant circulating through reservoir 110 from ambient air to allow greater temperature control of the liquid coolant circulating through liquid containment unit 100.

FIG. 7 is a greatly enlarged side elevational view of liquid containment unit 100 illustrating reservoir 110 and pump interface tube 112 in greater detail. As best shown by FIG. 7, reservoir 110 preferably comprises a sealed flexible bag including surface walls 140, end walls 142, partitions 144, flaps 146, inlet port 148, outlet port 150 and membrane 151. Surface walls 140 are preferably formed from a relatively thin, thermally conductive material such as polyurethane. Surface walls 140, end walls 142 and partitions 144 define a plurality of winding channels 152 which extend from inlet port 148 to outlet port 150. Channels 152 define a flow passage having an area larger than the cross-sectional area of water return line 96A. As a result, the flow rate of liquid coolant circulating through winding flow passages 152 of reservoir 110 is greatly reduced as it enters reservoir 110. Winding channels 152 cause the circulating liquid coolant to flow back and forth across the adjacent cooling plate 120 (shown in FIG. 6) to ensure that the liquid coolant circulates proximate to cooling plate 120 for a sufficient amount of time for allowing cooling plate 120 to adjust the temperature of the liquid coolant while also allowing cooling plate 120 and reservoir 110 to be compacted into a small area. Flaps 146 extend along a perimeter of reservoir 110 and define mounting detents 116.

Membrane 151 extends through one of surface walls 140 and communicates with winding channels 152. Membrane 151 is preferably formed from a gas permeable material which blocks the flow of liquids. As a result, membrane 151 allows air and other gases trapped within liquid containment unit 100 to escape while preventing the escape of the liquid coolant.

Reservoir 110 is preferably formed by heat sealing a pair of thin flexible sheets of plastic material such as polyurethane to one another to form seams along end walls 142 and partitions 144. Portions 154 and 156 of the plastic sheets are preferably heat sealed to one another about tubular insets 158, 159 to form inlet port 148 and outlet port 150, respectively. Apertures are punched through flaps 146 to form mounting detents 116. Similarly, an aperture is punched through one of the sheets to form a window in which membrane 151 is heat sealed. Due to its simple design and manufacture, the preferred embodiment of reservoir 110 is inexpensive and disposable. At the same time, reservoir 110 provides a sealed aseptic containment unit which allows the temperature of the liquid coolant circulating through reservoir 110 to be precisely adjusted by thermal conduction from cooling plate 120.

As best shown by FIG. 7, pump interface tube 112 preferably comprises a tube made of a flexible and compressible material such as poly vinyl chloride (PVC). The ends of the tube forming pump interface tube 112 are sealed to inset 159 extending from outlet port 150 and sensor interface module 104. Pump interface tube 112 preferably has a length sufficient for extending over and around roller pins 134 of pump 124. The tube of pump interface tube 112 preferably defines a lumen having a diameter of sufficient size to enable pump 124 (shown in FIG. 2) to pump the liquid coolant at a necessary flow rate through sensor interface module 104 and water feed line 94A through catheter 28. As can be appreciated other compressible interface structures, such as compressible bags, may be used in lieu of tube 112.

FIGS. 8 and 9 illustrate sensor interface module 104 in greater detail. FIG. 8 is a fragmentary side elevational view of liquid containment unit 100 illustrating sensor interface module 104 in greater detail. FIG. 9 is a cross-sectional view of sensor interface module 104 taken along lines 9—9 of FIG. 8. As best shown by FIGS. 8 and 9, sensor interface module 104 includes body 160, fitting 162, sealing bore 163, fill guide 164, fill plug 166, temperature interface 168 and pressure interface 170. Body 160 is a generally flat substantially rectangular structure which encircles and structurally supports temperature interface 168 and pressure interface 170 while defining a fluid chamber 172 adjacent to temperature interface 168 and pressure interface 170. Body 160 also preferably defines a pair of mounting detents 108 which stably and releasably support temperature interface 168 and pressure interface 170 adjacent temperature sensor 128 and pressure sensor 130 of sensor control unit 102 (shown in FIG. 6). Body 160 is preferably integrally formed and made from a translucent, rigid and lightweight material such as polycarbonate. As can be appreciated, body 160 may have any one of a variety of shapes and configurations and be made from any one of a variety of materials which enable body 160 to support a pressure interface between a fluid chamber and corresponding pressure and temperature sensors of a sensor control unit.

As best shown by FIG. 8, fluid chamber 172 includes two relatively flat, thin circular cavities 174 and 176 in fluid communication with one another. Cavity 174 is located adjacent to temperature interface 168 while cavity 176 is located adjacent to pressure interface 170. Cavity 174 has a shape corresponding to the shape of temperature interface 160 and is sized only slightly larger than the surface area of temperature sensor 168. Similarly, cavity 176 has a shape corresponding to the shape of pressure interface 170 and has an area only slightly larger than the surface area of pressure interface 170. Cavity 172 channels and directs the liquid coolant from pump interface tube 112 across pressure interface 170 and temperature interface 174 into water feed line 94A. At the same time, chamber 172 temporarily retains the liquid coolant as the temperature and pressure of the liquid coolant are sensed.

As further shown by FIGS. 8 and 9, housing 160 defines inlet port 180, outlet port 182 and fill port 184. Inlet port 180 extends through body 106 and provides communication between the interior of pump interface tube 112 and cavity 176. Outlet port 182 extends through body 160 and provides fluid communication between cavity 174 and the interior of water feed line 94A. Together, inlet port 180 and outlet port 182 permit liquid coolant to circulate through cavity 172 of sensor interface module 104. Fill port 184 extends through body 160 and provides communication with fluid chamber 172 for permitting liquid containment unit 100 to be filled and emptied with a supply of liquid coolant.

Sealing bore 163 and fitting 162 allow pump interface tube 112 and water feed line 94A to be coupled to body 160 in fluid communication with inlet 180 and outlet port 182, respectively. Fitting 162 preferably integrally projects from body 160 and is sized for mating with pump interface tube 112 to fluid connect pump interface tube 112 and inlet port 180. Sealing bore 163 extends into body 160 adjacent to outlet port 182. Sealing bore 163 receives water feed line 94A and allows water feed line 94A to sealingly mate with side walls of sealing bore 163 so as to provide fluid communication between the interior of water feed line 94A and outlet port 182.

Fill guide 164 is a generally rigid tubular member which defines a bore in fluid communication with fill port 184. Fill guide 164 receives a nozzle or another similar conventional fluid coupling of a fluid supply. For example, fill guide 164 preferably is sized for receiving a needle of a syringe through which fluid is supplied through fill port 184 into liquid containment unit 100. Once liquid containment unit 100 is adequately supplied with liquid coolant, fill guide 164 receives fill plug 166 which seals and blocks fill port 184.

Temperature interface 168 transmits liquid coolant temperature indicia from the liquid coolant circulating through chamber 172 to temperature sensor 128 (shown in FIG. 6). Temperature interface 168 allows temperature sensor 128 to indirectly determine the temperature of the liquid coolant within sensor interface module 104. Preferably, temperature interface 168 comprises a black body radiation emitter formed from a black body radiation emitting material such as anodized aluminum. Temperature interface 168 is fixed to and supported by body 160 adjacent to chamber 172. As conventionally known, black bodies emit radiation based upon their temperature. Because the liquid coolant circulating through chamber 172 contacts the black body radiation emitting material of temperature interface 168, the black body radiating emitting material emits radiation which corresponds to the temperature of the liquid coolant circulating through fluid chamber 172. Thus, temperature interface 168 allows the temperature of the liquid coolant to be indirectly sensed and measured.

Pressure interface 170 is fixed and supported by body 160 adjacent fluid chamber 172. Pressure interface 170 transmits pressure related indicia of the liquid coolant within fluid chamber 172 across pressure interface 170 to pressure sensor 130 (shown in FIG. 6) so that pressure sensor 130 may indirectly sense and determine the pressure and corresponding flow rate of the liquid coolant through chamber 172. Pressure interface 170 preferably comprises a flexible diaphragm made of polyurethane which is sealed to body 160 adjacent chamber 172. The flexible diaphragm expands and contracts based upon the pressure of the liquid coolant circulating through fluid chamber 172. As a result, the flexible diaphragm of pressure interface 170 allows pressure sensor 130 to sense the pressure exerted by the liquid coolant upon the flexible diaphragm to thereby detect the pressure of the liquid coolant circulating through chamber 172.

Figure 10:
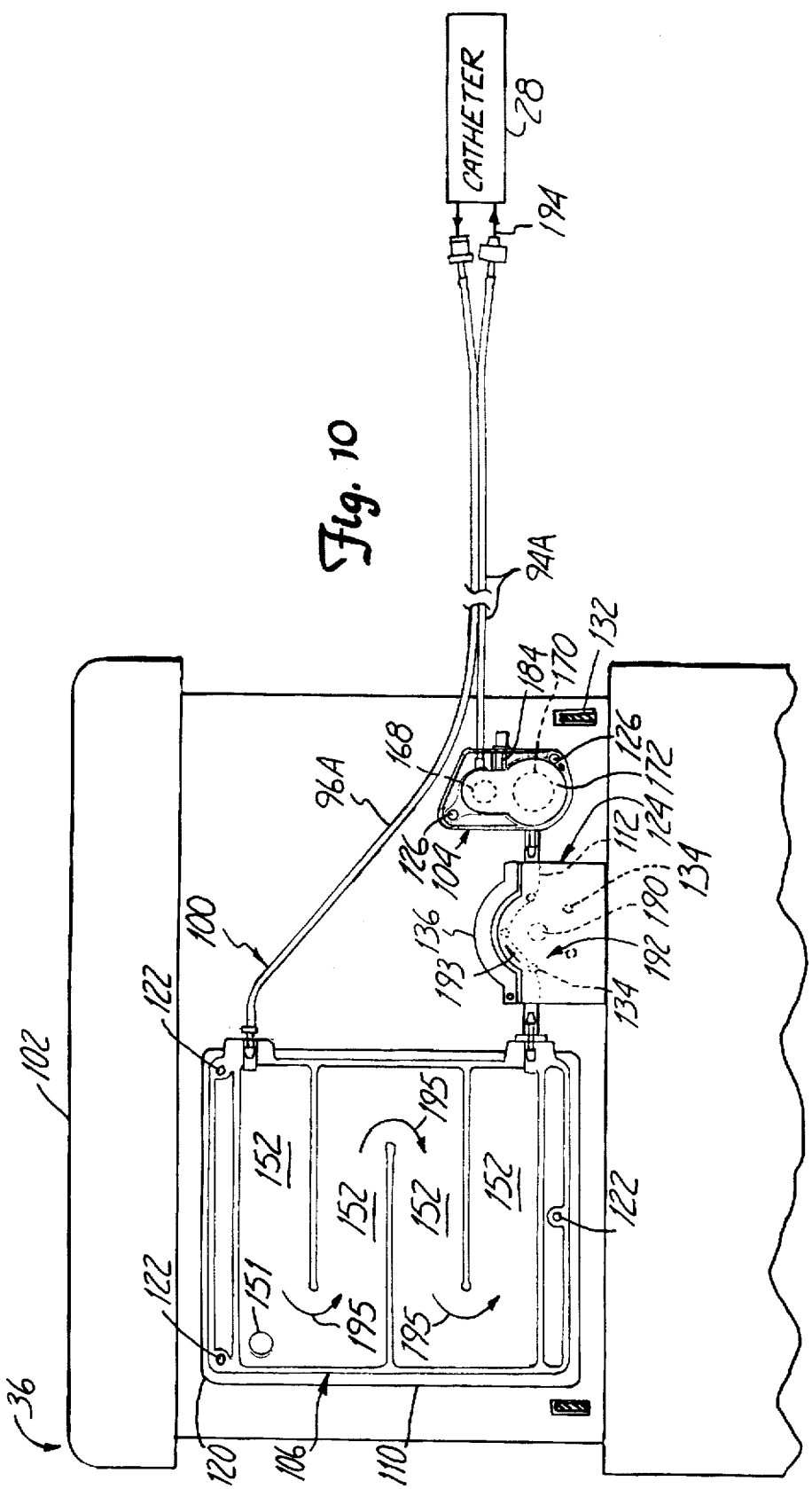
FIG. 10 is a side elevational view of liquid coolant supply system illustrating the liquid coolant containment unit supported adjacent to a sensor control unit.

FIG. 10 is a side elevational view of liquid coolant supply system 36 illustrating liquid coolant containment unit 100 removably supported adjacent to sensor control unit 102. For ease of illustration, portions of cover 132 are omitted. As best shown by FIG. 10, during treatment of BPH, temperature interface 168 and pressure interface 170 of sensor interface module 104 are removably supported adjacent to, and preferably in contact with, temperature sensor 128 and pressure sensor 130 of sensor control unit 102, respectively by mounts 126. Reservoir 110 of liquid coupling assembly 106 is removably supported adjacent to cooling plate 120 by mounts 122. Lastly, pump interface tube 112 is releasably and removably clamped and supported against roller pins 134 by jaw 136 of pump 124.

Once liquid coolant is supplied to liquid containment unit 100 and catheter 28 (shown in FIG. 2A) through fill port 184, the liquid coolant is circulated through catheter 28 and liquid containment unit 100 by rotation of roller pins 134 about axis 190 in the clockwise direction indicated by arrow 192. As a result, the liquid coolant moves in the direction indicated by arrow 193 through pump interface tube 112. The liquid fluid continues to circulate into fluid chamber 172 adjacent to pressure sensor 170 and temperature sensor 168 and through water feed line 94A to catheter 28 as indicated by arrow 194. After the liquid coolant has circulated through catheter 28, the liquid coolant is returned to liquid coolant supply system 100 through water return line 96A. The returning liquid coolant continues to circulate through channels 152 within reservoir 110 adjacent to cooling plate 120 as indicated by arrows 195. As the liquid coolant circulates through channels 152 adjacent to cooling plate 120, the liquid coolant is chilled by thermal plate 120. Due to winding channels 152, the liquid coolant flows adjacent to thermal plate 120 for a sufficient period of time to sufficiently decrease or increase the temperature of the liquid coolant as necessary. In addition, winding channels 152 also enable reservoir 110 and thermal plate 120 to be compact and thermally efficient. Any gases trapped within liquid containment unit 106 are permitted to escape through membrane 151 within reservoir 110.

Once the liquid coolant enters fluid chamber 172 of sensor interface module 104, the liquid coolant accumulated within fluid chamber 172 exerts a force against the diaphragm of pressure interface 170. In response, the diaphragm expands against pressure sensor 130 (shown in FIG. 6). Pressure sensor 130 senses the pressure exerted upon it by diaphragm 170 and determines the pressure of the liquid coolant within fluid chamber 172 of sensor interface module 104. From a determined pressure, the flow rate of the liquid coolant through sensor interface module 104 and through liquid containment unit 106 may be determined by sensor control unit 102.

At essentially the same time, the liquid coolant temporarily contained within fluid chamber 172 thermally conducts or withdraws heat to or from the black body material forming temperature interface 168. Temperature interface 168 emits a corresponding radiation which is sensed by the infrared radiation sensor of temperature sensor 128 (shown in FIG. 6). Sensor control unit 102 determines the temperature of the liquid coolant within sensor interface control module 104 based upon the sensed level of radiation detected by temperature sensor 128.

Liquid coolant supply system 102 permits closed-loop control of the temperature and pressure of the liquid coolant being pumped and circulated through catheter 28. Thermal plate 120 adjusts the temperature of the liquid coolant flowing through reservoir 110. Almost immediately after leaving reservoir 110, the liquid cooling is pumped by pump 124 into sensor interface module 104. Sensor interface module 104 allows sensor control unit 102 to indirectly sense and determine both the pressure correlating to flow rate and the temperature of the liquid coolant immediately before the liquid coolant is pumped through water feed line 94A into and through catheter 28. Temperature sensor 128 and pressure sensor 130 of sensor control unit 102 provide signals to sensor control unit 102 which represent or correspond to the temperature and the pressure (corresponding to flow rate) of the liquid coolant. Using the data representing the temperature and pressure of the liquid coolant within sensor interface module 104, sensor control unit 102 adjusts both the temperature of thermal plate 120 and the rotational speed of roller pins 134 about axis 190 to adjust both the temperature and the flow rate of the liquid coolant circulating through liquid containment unit 100. As a result of the closed-loop feedback between sensor interface module 104 and sensor control unit 102, liquid coolant supply system 100 is capable of almost instantaneous adjustment of the temperature and flow rate of the liquid coolant. In addition, sensor control unit 102 preferably receives electrical signals and data from microwave source 38, urethral thermometry unit 39 and a rectal thermometry unit (not shown) to further regulate the temperature and flow rate of the liquid coolant supplied by liquid coolant supply system 102 and being circulated through catheter 28.

Once treatment of the BPH by thermal therapy has been completed, sensor control unit 102 may be readied for treatment of another patient by simply opening door 32, lifting jaw 136 and sliding reservoir 110 and temperature interface module 104 off of registered pins 122 and 126, respectively, to remove the used liquid containment unit 100 for disposal or cleaning. A pre-cleaned fresh liquid containment unit 100 may be likewise simply mounted to sensor control unit 102 and supplied with liquid coolant for treatment of another patient.

Although the present invention has been described with reference to preferred embodiments, workers skilled in the art will recognize that changes may be made in form and detail without departing from the spirit and scope of the invention.

What is claimed is:

1. A coolant-sensor interface module for enabling temperature and pressure of a liquid coolant within a thermal therapy catheter fluid supply system to be sensed by a temperature sensor and a pressure sensor without direct contact of the liquid coolant with the temperature sensor and the pressure sensor, the module comprising:

a body having a fluid chamber with an inlet port and an outlet port for allowing the liquid coolant to circulate through the fluid chamber;

a temperature interface supported adjacent the fluid chamber within the body, wherein the temperature interface communicates a temperature indicant of the liquid coolant circulating through the fluid chamber to the temperature sensor which is external to the body and not in direct contact with the liquid coolant; and a pressure interface supported adjacent the fluid chamber within the body, wherein the pressure interface communicates a pressure indicant of the liquid coolant circulating through the fluid chamber to the pressure sensor which is external to the body and not in direct contact with the liquid coolant.

2. The module of claim 1 wherein the temperature interface includes:
a radiation emitter adjacent the fluid chamber for emitting radiation corresponding to the temperature of the liquid coolant circulating through the fluid chamber.

3. The module of claim 1 wherein the pressure interface includes:
a flexible diaphragm supported adjacent the fluid chamber, wherein the flexible diaphragm expands based upon the pressure of the liquid coolant circulating through the fluid chamber.

4. The module of claim 1 including:
a fill port extending through the body for permitting liquid coolant to be supplied to the interface module; and
means for sealing the fill port.

5. The module of claim 1 including:
mounting detents for releasably mounting the temperature interface adjacent the temperature sensor and the pressure interface adjacent the pressure sensor.

6. A liquid coolant containment unit for use with a thermal therapy catheter, the containment unit comprising:
a coolant-sensor interface module including:
a body having a fluid chamber with an inlet port and an outlet port for allowing a liquid coolant to circulate through the fluid chamber;
a temperature interface supported adjacent the fluid chamber within the body, wherein the temperature interface communicates a temperature indicant of the liquid coolant circulating through the fluid chamber to a temperature sensor; and
a pressure interface supported adjacent the fluid chamber within the body, wherein the pressure interface communicates a pressure indicant of the liquid coolant circulating through the fluid chamber to a pressure sensor; and
a liquid coupling assembly for fluidly connecting the coolant-sensor interface module to input and output ports of the thermal therapy catheter and for containing the liquid coolant as the liquid coolant is cooled and pumped by cooling and pumping means.

7. The module of claim 6 wherein the temperature interface includes:
a radiation emitter adjacent the fluid chamber for emitting radiation corresponding to the temperature of the liquid coolant circulating through the fluid chamber.

8. The module of claim 6 wherein the pressure interface includes:
a flexible diaphragm supported adjacent the fluid chamber, wherein the flexible diaphragm expands based upon the pressure of the liquid coolant circulating through the fluid chamber.

9. The containment unit of claim 6 wherein the liquid coupling assembly includes a sealed reservoir including an inlet port and an outlet port, wherein the reservoir directs liquid flow adjacent the cooling means.

10. The containment unit of claim 9 wherein the sealed reservoir includes mounting detents for releasably supporting the sealed reservoir adjacent the cooling means.

11. The containment unit of claim 9 wherein the sealed reservoir comprises a thin thermally conducting bag.

12. The containment unit of claim 9 wherein the reservoir includes a plurality of winding channels for channeling liquid flow adjacent the cooling means.

13. The containment unit of claim 9 wherein the sealed reservoir includes:
a gas permeable membrane for permitting gas to escape from the sealed reservoir while preventing liquid coolant from escaping from the sealed reservoir.

14. The containment unit of claim 6 wherein the liquid coupling assembly includes:
a pump interface for containing and isolating the liquid coolant from the pumping means and for communicating pressure from the pumping means to the liquid coolant to circulate the liquid coolant.

15. A liquid coolant supply system for supplying a liquid coolant to a thermal therapy catheter, the system comprising:
a sensor control unit including:
a pump;
a cooling device;
a temperature sensor; and
a pressure sensor; and
a liquid coolant containment unit including:
a coolant-sensor interface module including:
a body having a fluid chamber with an inlet port and an outlet port for allowing the liquid coolant to circulate through the fluid chamber;
a temperature interface supported adjacent the fluid chamber within the body, wherein the temperature interface communicates a temperature indicant of the liquid coolant circulating through the fluid chamber to the temperature sensor; and
a pressure interface supported adjacent the fluid chamber within the body, wherein the pressure interface communicates a pressure indicant of the liquid coolant circulating through the fluid chamber to the pressure sensor;
fluid coupling means for fluidly connecting the sensor interface module to inlet and outlet ports of the thermal therapy catheter; and
means for removably supporting the fluid coupling means adjacent the cooling device and the pump, the temperature interface adjacent the temperature sensor and the pressure interface adjacent the pressure sensor so that the liquid coolant containment unit may be replaced with another liquid cooling containment unit.

16. The supply system of claim 14 wherein the temperature interface comprises a radiation emitter which emits radiation corresponding to a temperature of the liquid coolant and wherein the temperature sensor comprises an infrared radiation sensor.

17. The supply system of claim 14 wherein the pressure interface comprises a flexible diaphragm which expands based upon the pressure of the liquid coolant circulating through the sensor interface module.

18. The supply system of claim 14 wherein the fluid coupling means includes a flexible compressible fluid conduit and wherein the pump comprises a peristaltic pump which dynamically compresses the fluid conduit to pump the liquid coolant through the fluid conduit to circulate the liquid coolant.

19. The supply system of claim 14 including:
means for controlling the cooling device based upon temperature sensed by the temperature sensor; and
means for controlling the pump based upon pressure sensed by the pressure sensor.

20. A liquid coolant supply system for supplying a liquid coolant to a thermal therapy catheter, the system comprising:
a sensor control unit including:
a temperature sensor;

a pressure sensor;

a peristaltic pump, wherein the pump pumps the coolant at a rate based upon sensed pressure signals from the pressure sensor; and a cooling plate, wherein the cooling plate has a temperature which varies based upon sensed signals from the infrared sensor; and liquid coolant containment unit including:

a liquid reservoir configured for being removably supported adjacent the cooling plate, wherein the reservoir contains and channels the liquid coolant adjacent the cooling plate to cool the liquid coolant;

a coolant-sensor interface module including:

a body having a fluid chamber with an inlet port and an outlet port for allowing the liquid coolant to circulate through the fluid chamber;

a temperature interface supported adjacent the fluid chamber within the body, wherein the temperature interface communicates a temperature indicant of the liquid coolant circulating through the fluid chamber to the temperature sensor;

a pressure interface supported adjacent the fluid chamber within the body, wherein the pressure interface communicates a pressure indicant of the liquid coolant circulating through the fluid chamber to the pressure sensor;

a compressible tube in fluid connection with the reservoir and the sensor interface module, the flexible tube configured for being positioned adjacent the pump so that actuation of the pump pumps and circulates the liquid coolant through the liquid coolant containment unit; and a liquid coupling assembly for fluidly connecting the liquid reservoir, the coolant-sensor interface module and the compressible tube to input and output ports of the thermal therapy catheter.

* * * * *

UNITED STATES PATENT AND TRADEMARK OFFICE
CERTIFICATE OF CORRECTION

PATENT NO. : 5,733,319
DATED : MARCH 31, 1998
INVENTOR(S) :
Bruce H. Neilson et al.

It is certified that error appears in the above-identified patent and that said Letters Patent is hereby corrected as shown below:

On the Title page, Col. 2, insert --*Attorney, Agent, or Firm*-Kinney & Lange, P.A.--

Col. 4, Line 45, delete "tureen" and insert --lumen--

Col. 4, Line 57, delete "Dow Coming" and insert --Dow Corning--

Col. 5, Line 50 delete "tureens" and insert --lumens--

Signed and Sealed this

Thirty-first Day of August, 1999

Attest:

Q. TODD DICKINSON

*Attesting Officer*     *Acting Commissioner of Patents and Trademarks*